United States Patent
Sah (10) Patent No.: US 11,135,178 B2
(45) Date of Patent: Oct. 5, 2021

(54) THYMOL AND CARVACOL FOR USE IN MEDICINE

(71) Applicant: UNIVERSITY OF IOWA RESEARCH FOUNDATION, Iowa City, IA (US)

(72) Inventor: Rajan Sah, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 531 days.

(21) Appl. No.: 15/509,438

(22) PCT Filed: Sep. 11, 2015

(86) PCT No.: PCT/US2015/049685
§ 371 (c)(1),
(2) Date: Mar. 7, 2017

(87) PCT Pub. No.: WO2016/040801
PCT Pub. Date: Mar. 17, 2016

(65) Prior Publication Data
US 2017/0326075 A1 Nov. 16, 2017

Related U.S. Application Data

(60) Provisional application No. 62/049,139, filed on Sep. 11, 2014.

(51) Int. Cl.
*A61K 31/05* (2006.01)
*A61P 21/00* (2006.01)

(52) U.S. Cl.
CPC .................................... *A61K 31/05* (2013.01)

(58) Field of Classification Search
CPC ................................. A61K 31/05; A61P 21/00
See application file for complete search history.

(56) References Cited

U.S. PATENT DOCUMENTS

| | | | |
|---|---|---|---|
| 5,599,561 A | 2/1997 | Gonzalez | |
| 9,044,390 B1 | 6/2015 | Speier et al. | |
| 2006/0171945 A1* | 8/2006 | Critchley | A61K 31/00 424/145.1 |
| 2006/0188588 A1* | 8/2006 | Zoorob | A61K 36/23 424/745 |
| 2011/0281956 A1 | 11/2011 | Park | |
| 2013/0018102 A1 | 1/2013 | Dente et al. | |

FOREIGN PATENT DOCUMENTS

| | | |
|---|---|---|
| EP | 2277395 A1 | 1/2011 |
| FR | 2872683 A1 | 1/2006 |
| WO | 2010019034 A1 | 2/2010 |

OTHER PUBLICATIONS

Nauffal ("Influence of recent immobilization and recent surgery on mortality in patients with pulmonary embolism", Journal of Thrombosis and Haemostasis (Sep. 2012); vol. 10, Issue9: pp. 1752-1760). (Year: 2010).*

Cho, et al., "Differential effects of low-dose resveratrol on adiposity and hepatic steatosis in diet-induced obese mice", British Journal of Nutrition 108, 2166-2175 (2012).

Ezhumalai, et al., "Antihyperglycemic effect of carvacrol in combination with rosiglitazone in high-fat diet-induced type 2 diabetic C57BL/6J mice", Molecular and Cellular Biochemistry 385, 23-31 (2014).

Greaser, et al., "Effects of diethyl ether and thymol on the ultrastructural and biochemical properties of purified sarcoplasmic reticulum fragments from skeletal muscle", Biochimica et Biophysica Acta (BBA)—Biomembranes 193(1), 73-81 (1969).

Kim, et al., "Carvacrol Protects against Hepatic Steatosis in Mice Fed a High-Fat Diet by Enhancing SIRT1-AMPK Signaling", Evidence-Based Complementary and Alternative Medicine (2013).

Narkar, et al., "AMPK and PPARδ agonists are exercise mimetics", Cell 134(3), 405-415 (2008).

Patent Cooperation Treaty, International Searching Authority, Search Report and Written Opinion for PCT/US2015/049685, 18 pages, dated Mar. 1, 2016.

Ruas, et al., "A PGC-1a Isoform Induced by Resistance Training Regulates Skeletal Muscle Hypertrophy", Cell 151, 1319-1331 (2012).

Szentesi, et al., "Altered Elementary Calcium Release Events and Enhanced Calcium Release by Thymol in Rat Skeletal Muscle", Biophys J 86(3), 1436-1453 (2004).

Ye, et al., "Beige Adipocytes Are a Distinct Type of Thermogenic Fat Cell in Mouse and Human", Cell 150(2), 366-376 (2012).

* cited by examiner

Primary Examiner — Jeffrey S Lundgren
Assistant Examiner — Chris E Simmons
(74) Attorney, Agent, or Firm — Viksnins Harris Padys Malen LLP (57) ABSTRACT

The invention provides therapeutic methods comprising the administration of thymol or carvacrol, or a pharmaceutically acceptable salt or prodrug thereof. The methods are useful for modulating muscle atrophy, performance, recovery, generation, or maintenance in animals.

9 Claims, 9 Drawing Sheets

Specification includes a Sequence Listing.

# THYMOL AND CARVACOL FOR USE IN MEDICINE

RELATED APPLICATION

This application claims the benefit of priority of U.S. Provisional Application Ser. No. 62/049,139 filed on Sep. 11, 2014, which application is herein incorporated by reference.

SEQUENCE LISTING

The instant application contains a Sequence Listing which has been filed electronically in ASCII format and is hereby incorporated by reference in its entirety. Said ASCII copy, created on Jul. 25, 2017, is named 17023_153US1_SL.txt and is 4,964 bytes in size.

BACKGROUND

Thymol (2-isopropyl-5-methylphenol, IPMP) is a natural monoterpene phenol found predominantly in oil of thyme, and extracted from *Thymus vulgaris* (common thyme) and various other kinds of plants. Thymol provides the distinctive, strong flavor of the culinary herb thyme (made from *T. vulgaris*) and is present in other spices, as well.

Thymol is part of a naturally occurring class of compounds known as biocides, with strong antimicrobial attributes. Biocides are a class of compounds shown to have antimicrobial and antifungal properties. Thymol has been used in alcohol solutions and in dusting powders for the treatment of tinea or ringworm infections, and was used in the US to treat hookworm infections. It is also used as a preservative in halothane, an anesthetic, and as an antiseptic in mouthwash. When used to reduce plaque and gingivitis, thymol has been found to be more effective when used in combination with chlorhexidine than when used purely by itself.

Carvacrol (2-methyl-5-isopropylphenol) is a natural monoterpene phenol found in oregano, which gives the spice its characteristic odor. Carvacrol is also known for its antibacterial properties. Its low toxicity together with its pleasant taste and smell suggests its use as a food additive to prevent bacterial contamination. It is a potent activator of the human ion channels transient receptor potential V3 (TRPV3) and A1 (TRPA1). Application of carvacrol on the human tongue, as well as activation of TRPV3, causes a sensation of warmth. In addition, carvacrol also activates, but then rapidly desensitizes, the pain receptor TRPA1; this explains its pungency. Carvacrol has also been shown to be protective in obesity (Cho S, et.al. *J Nutri Biochem* 2012) and diabetes (Ezhumalai M. et al. *Mol Cell Biochem* 2014) in mouse models, though the mechanisms remain unclear.

Muscle loss/atrophy is a condition associated with several causes, such as aging (sarcopenia), cancer and other diseases (cachexia), chronic illness/immobilization and poor nutrition. Muscle atrophy occurs by a change in the normal balance between protein synthesis and protein degradation. During atrophy, there is a down-regulation of protein synthesis pathways, and an activation protein degradation. Loss of muscle is a result of diverse conditions and is typically a signal of poor outcomes for a number of conditions. The preservation of muscle aids in patient survival and recovery as well as overall well-being.

Currently there is a need for agents that are useful to: 1) enhance skeletal muscle endurance and performance in sedentary patients and in the elderly; 2) prevent skeletal muscle atrophy in the chronically ill or immobilized; 3) improve overall metabolic health by increasing basal metabolic rate via increased lean body weight and reduced adiposity in the obese; or 4) prevent the negative effects of prolonged space flight on skeletal muscle (atrophy).

Additionally, obesity is a major public health problem in the United States and world-wide, predisposing to systemic inflammation which culminates in diabetes, heart disease, pulmonary disease and arthritis—resulting in a huge burden of disease and disability. Regular exercise and maintenance of muscle endurance and lean muscle mass are known to have significant beneficial metabolic effects in these conditions. There is also currently a need for compounds that can substitute for exercise, or significantly enhance the effects of mild, relatively sedentary activity to increase muscle endurance, metabolic rate, lean muscle mass and counter obesity.

SUMMARY

It has been discovered that thymol and carvacrol increase calcium cycling in skeletal muscle (both C2C12 myotubes and isolated primary mouse muscle fibers) by activating either TRPV3 ion channels and/or via activation of the sarcoplasmic reticulum calcium release channel. In C2C12 myotubes, these compounds increase myotube size and increase the expression of genes associated with mitochondrial biogenesis, oxidative metabolism and muscle endurance. In vivo, it has been determined that sedentary mice supplemented with Thymol for 5 weeks have a significantly improved exercise capacity, increased muscle mass and enhanced thermogenesis compared to vehicle treated mice.

Accordingly these compounds can be used to: 1) enhance skeletal muscle endurance and performance in sedentary patients and in the elderly; 2) prevent skeletal muscle atrophy in the chronically ill or immobilized; 3) improve overall metabolic health by increasing basal metabolic rate via increased lean body weight and reduced adiposity in the obese; or 4) prevent the negative effects of prolonged space flight on skeletal muscle (atrophy).

The compounds thymol and carvacrol are also useful as substitutes for exercise, to enhance the effects of mild, relatively sedentary activity, or to increase muscle endurance, metabolic rate, or lean muscle mass, or to counter obesity.

In one embodiment the invention provides a method comprising modulating muscle atrophy, performance, recovery, generation, or maintenance in an animal in need thereof by administering thymol or carvacrol, or a pharmaceutically acceptable salt or prodrug thereof to the animal. In one embodiment the invention provides a method comprising restoring diaphragm endurance or strength to assist in extubation of a mechanically ventilated patient by administering thymol or carvacrol, or a pharmaceutically acceptable salt or prodrug thereof to the patient. In one embodiment the invention provides a method comprising enhancing muscular recovery in a rehabilitating patient in need thereof by administering thymol or carvacrol, or a pharmaceutically acceptable salt or prodrug thereof to the patient.

In one embodiment the invention provides a method comprising increasing lean body mass, increasing metabolic rate, or promoting fat weight loss in an animal in need thereof by administering thymol or carvacrol, or a pharmaceutically acceptable salt or prodrug thereof to the animal.

In one embodiment the invention provides a method comprising improving the effects of exercise on muscle endurance or muscle mass in an animal in need thereof by administering thymol or carvacrol, or a pharmaceutically acceptable salt or prodrug thereof to the animal.

In one embodiment the invention provides a method comprising promoting weight loss in an animal in need thereof by administering thymol or carvacrol, or a pharmaceutically acceptable salt or prodrug thereof to the animal.

In one embodiment the invention provides a pharmaceutical composition comprising thymol or carvacrol, or a pharmaceutically acceptable salt or prodrug thereof, formulated for administration to modulate muscle atrophy, performance, recovery, generation, or maintenance in an animal.

In one embodiment the invention provides a kit comprising: 1) packaging material, 2) thymol or carvacrol, or a pharmaceutically acceptable salt or prodrug thereof, and 3) instructions for administering the thymol, carvacrol, pharmaceutically acceptable salt, or prodrug to an animal to modulate muscle atrophy, performance, recovery, generation, or maintenance.

In one embodiment the invention provides thymol or carvacrol, or a pharmaceutically acceptable salt or prodrug thereof for modulating muscle atrophy, performance, recovery, generation, or maintenance.

In one embodiment the invention provides thymol or carvacrol, or a pharmaceutically acceptable salt or prodrug thereof for restoring diaphragm endurance or strength to assist in extubation.

In one embodiment the invention provides thymol or carvacrol, or a pharmaceutically acceptable salt or prodrug thereof for enhancing muscular recovery.

In one embodiment the invention provides thymol or carvacrol, or a pharmaceutically acceptable salt or prodrug thereof for increasing lean body mass, increasing metabolic rate, or promoting fat weight loss.

In one embodiment the invention provides thymol or carvacrol, or a pharmaceutically acceptable salt or prodrug thereof for improving the effects of exercise on muscle endurance or muscle mass.

In one embodiment the invention provides thymol or carvacrol, or a pharmaceutically acceptable salt or prodrug thereof for promoting weight-loss.

In one embodiment the invention provides the use of thymol or carvacrol, or a pharmaceutically acceptable salt or prodrug thereof to prepare a medicament for modulating muscle atrophy, performance, recovery, generation, or maintenance in an animal in need thereof.

In one embodiment the invention provides the use of thymol or carvacrol, or a pharmaceutically acceptable salt or prodrug thereof to prepare a medicament for restoring diaphragm endurance or strength to assist in extubation of a mechanically ventilated patient.

In one embodiment the invention provides the use of thymol or carvacrol, or a pharmaceutically acceptable salt or prodrug thereof to prepare a medicament for enhancing muscular recovery in a rehabilitating patient.

In one embodiment the invention provides the use of thymol or carvacrol, or a pharmaceutically acceptable salt or prodrug thereof to prepare a medicament for increasing lean body mass, increasing metabolic rate, or promoting fat weight loss in an animal in need thereof.

In one embodiment the invention provides the use of thymol or carvacrol, or a pharmaceutically acceptable salt or prodrug thereof to prepare a medicament for improving the effects of exercise on muscle endurance or muscle mass in an animal in need thereof.

In one embodiment the invention provides the use of thymol or carvacrol, or a pharmaceutically acceptable salt or prodrug thereof to prepare a medicament for promoting weight loss in an animal in need thereof.

In one embodiment the invention provides a method for treating a disease or condition in an animal wherein activation of the sarcoplasmic reticulum calcium release channel is indicated comprising administering thymol or carvacrol, or a pharmaceutically acceptable salt or prodrug thereof to the animal.

In one embodiment the invention provides a method for activating a sarcoplasmic reticulum calcium release channel in an animal in need thereof comprising administering thymol or carvacrol, or a pharmaceutically acceptable salt or prodrug thereof to the animal.

DETAILED DESCRIPTION

Thymol and carvacrol are naturally occurring compounds that are commercially available or that can be isolated from natural sources.

Thymol and carvacrol can also be administered as pharmaceutically acceptable salts. Pharmaceutically acceptable salts may be obtained using standard procedures well known in the art, for example by reacting a sufficiently acidic compound such as an alcohol with a suitable base affording a physiologically acceptable cation.

In addition to the administration of salt forms, thymol and carvacrol can also be administered in a prodrug form. Prodrugs of thymol and carvacrol can be prepared from the natural products using standard procedures.

In one embodiment the disease or condition wherein activation of the sarcoplasmic reticulum calcium release channel is indicated is sarcopenia.

The term "prodrug" refers to those compounds that undergo chemical changes under physiological conditions to provide thymol or carvacrol or a salt thereof. Additionally, prodrugs can be converted to thymol or carvacrol or a salt thereof by chemical or biochemical methods in an ex vivo environment. For example, prodrugs can be slowly converted to thymol or carvacrol or a salt thereof when placed in a transdermal patch reservoir with a suitable enzyme or chemical reagent.

Prodrugs of the invention include compounds wherein a hydroxyl group of thymol or carvacrol is converted into a group such as, but not limited to, an ester, a phosphate ester, a hemisuccinate, a dimethylaminoacetate, or a phosphoryloxymethyloxy-carbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxyl groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxy group of the hemiacetal form of a carbohydrate).

For additional examples of prodrugs, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents, for example, other agents that are useful to modulate muscle atrophy, performance, recovery, generation, or maintenance.

The invention will now be illustrated by the following non-limiting Examples.

Example 1

Figure 1:
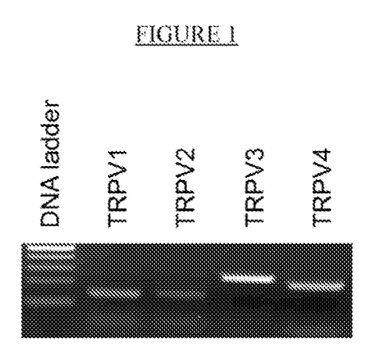
FIG. 1. RT-PCR of TRPV1-4 in skeletal muscle.

Transient Receptor Potential Vanilloid (TRPV) channels are broadly expressed and represent novel pathways for enhancing $Ca^{2+}$ cycling in tissues important for whole body metabolism, including adipose tissue (Ye, L., et al., *Cell*, 2012, 151(1), 96-110) and skeletal muscle (Ito, N., et al., *Nat Med*, 2013, 19(1), 101-1066; and Luo, Z., et al., *Cell Res*, 2012, 22(3), 551-64). Consistent with the data shown in FIG. 1, previously published transcriptional studies reveal mRNA expression of TRPV1 through 4 in murine and human skeletal muscle, with TRPV3 expression highest (Kunert-Keil, C., et al., *BMC Genomics*, 2006, 7, 159). RT-PCR of TRPV1-4 in skeletal muscle as shown in FIG. 1 was performed from skeletal muscle as described previously (Sah R., et al., The Timing of Myocardial Trpm7 Deletion during Cardiogenesis Variably Disrupts Adult Ventricular Function, Conduction and Repolarization. Circulation. 2013; Sah R., et al., Ion channel-kinase TRPM7 is required for maintaining cardiac automaticity. Proc Natl Acad Sci USA. 2013; 110:E3037-46) using the following primers:

```
                                      (SEQ ID NO: 1)
    mATF3-F:  GCTGCCAAGTGTCGAAACAAG (SEQ ID NO: 2)
    mATF3-R:  CAGITITCCAATGGCTTCAGG (SEQ ID NO: 3)
    mHKII-F:  CAAGCGTGGACTGCTCTTCC (SEQ ID NO: 4)
    mHKII-R:  TGTTGCAGGATGGCTCGGAC (SEQ ID NO: 5)
    mPGC la-F:  AGCCGTGACCA CTGACAACGAG (SEQ ID NO: 6)
    mPGC 1-a-R:  GCTGCATGGTTCTGAGTGCTAAG (SEQ ID NO: 7)
    mMSTN-F:  AGTACGACGTCCAGAGGGAT (SEQ ID NO: 8)
    mMSTN-R:  TTGCCATCCGCTTGCA TTAG (SEQ ID NO: 9)
    mIGF-1-F:  GCGATGGGGAAAA TCAGCAG (SEQ ID NO: 10)
    mIGF-1-R:  CGCCAGGTAGAAGAGGTGTG (SEQ ID NO: 11)
    mSkActin-F:  TCCAAGTCCTGCAAGTGAACA (SEQ ID NO: 12)
    mSkActin-R:  GTCAGGATACCTCGCTTGCT.
```

Figure 2:
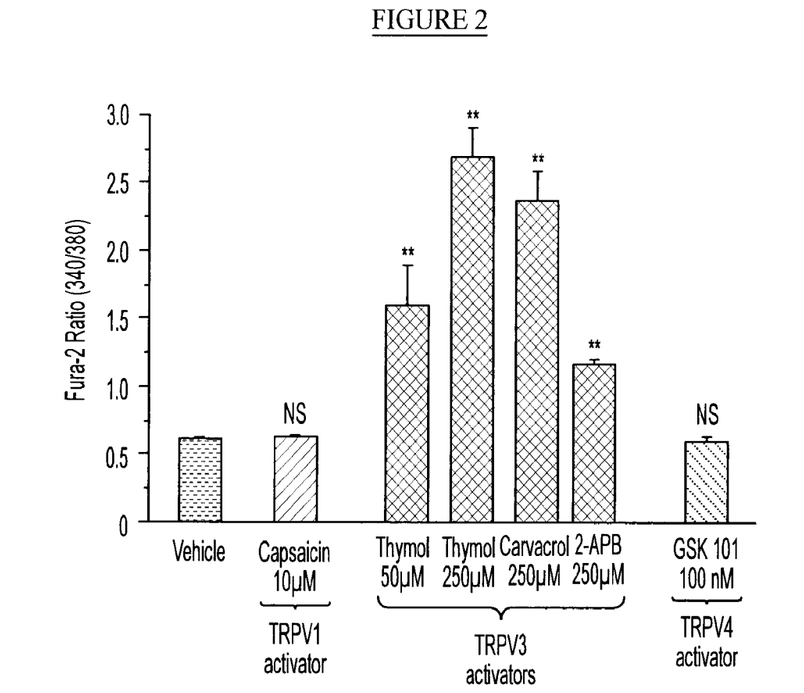
FIG. 2. Fura-2 $Ca^{2+}$ Ratios in C2C12 myotubes in response to known activators of TRPV1 (Capsaicin), TRPV3 (Thymol, Carvacrol, 2-APB), and TRPV4 (GSK 101). ** $p<0.01$ compared to vehicle $Ca^{2+}$ response.

To determine the physiological significance of these TRPV ion channels in skeletal muscle $Ca^{2+}$ homeostasis, a functional screen for the magnitude of intracellular $Ca^{2+}$ rise was performed using known agonists for TRPV1 (Capsaicin), TRPV3 (Carvacrol/Thymol/2-APB) and TRPV4 (GSK101) in C2C12 myotubes (FIG. 2). C2C12 myoblasts were grown to confluency and then differentiated into myotubes by culturing in Dulbecco's Modified Eagles Medium (DMEM) with 2% horse serum for 5 days. Measurement of Fura-2 Ca2+ ratios in C2C12 myotubes was performed as described previously in cultured adipocytes (Ye L., et al., TRPV4 is a regulator of adipose oxidative metabolism, inflammation, and energy homeostasis. *Cell*. 2012; 151:96-110). It was found that only TRPV3 agonists induced reproducible and reversible increases in cytosolic $Ca^{2+}$, while TRPV1 and TRPV4 agonists had essentially no effect on intracellular $Ca^{2+}$.

Figure 3:
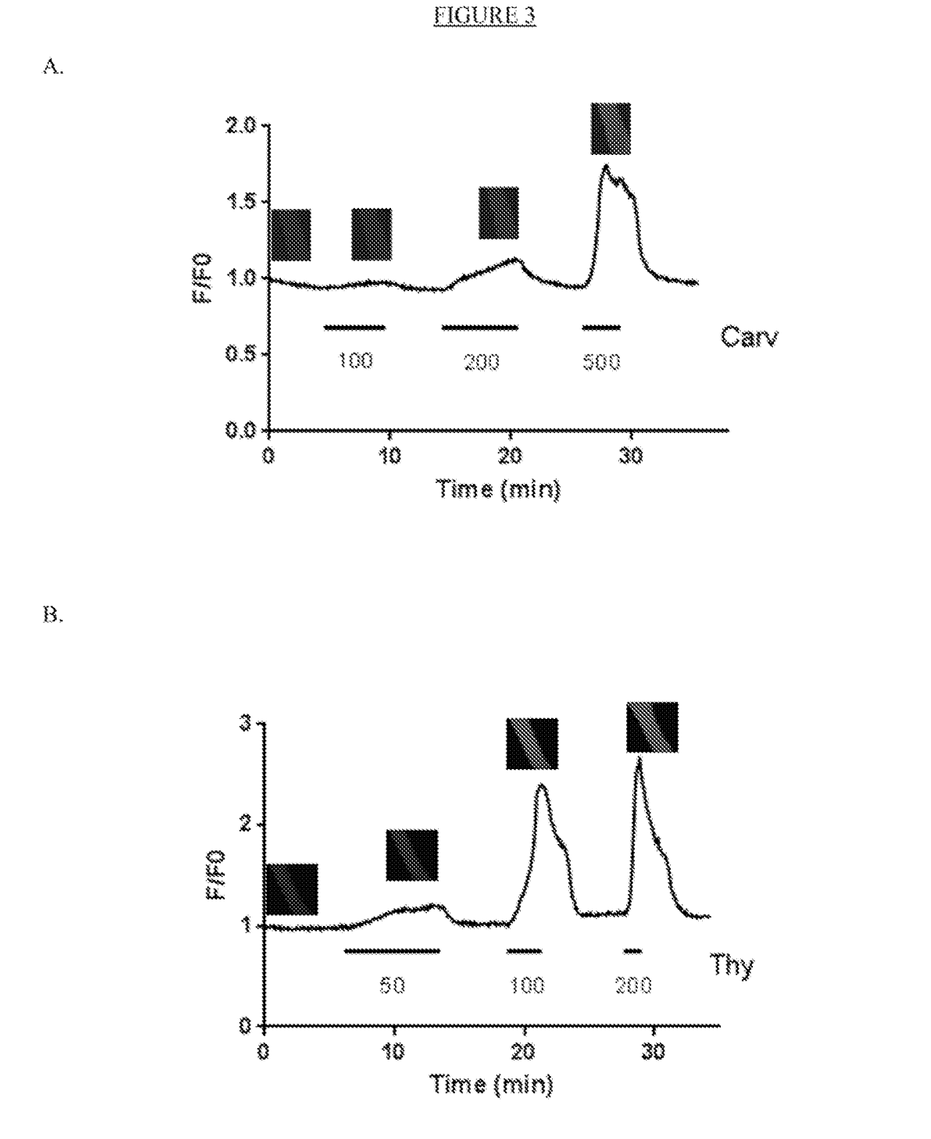
FIG. 3. Confocal calcium imaging (Fluo-4AM) of freshly isolated mouse flexor digitorum brevis (FDB) muscle fibers in response to sequential applications of carvacrol (A: 100, 200 and 500 µM) and thymol (B: 50, 100 and 200 µM). Inset shows confocal image of the FDB muscle fiber during the experiment.

These findings were further validated in freshly isolated mouse flexor digitorum brevis (FDB) muscle fibers (FIG. 3) to confirm the result in primary muscle cells. Primary skeletal muscle fibers were isolated from flexor digitorum brevis (FDB) muscle. In brief, FDB muscles were dissected and mechanically cleaned of connective tissue in a standard Ringer's solution containing (in mM): 146 NaCl, 5 KCl, 2 CaCl2, 1 MgCl2, and 10 HEPES, pH 7.4 with NaOH. Muscles were then shaken for 40 min at 37° C. in 1 mg/ml of collagenase A (Roche) dissolved in Ringer's solution. After collagenase treatment, individual FDB fibers were dissociated by gentle trituration using Pasteur pipettes of decreasing bore size. Only fibers exhibiting clear striations and clean surfaces were chosen for electrophysiological recordings. All experiments were conducted at room temperature on fibers obtained within 8 h of isolation. Confocal calcium imaging of FDB fibers were performed as described previously in cardiac myocytes but at room temperature (23° C.) (Sah R., et al., Ion channel-kinase TRPM7 is required for maintaining cardiac automaticity. Proc Natl Acad Sci USA. 2013; 110:E3037-46).

Figure 4:
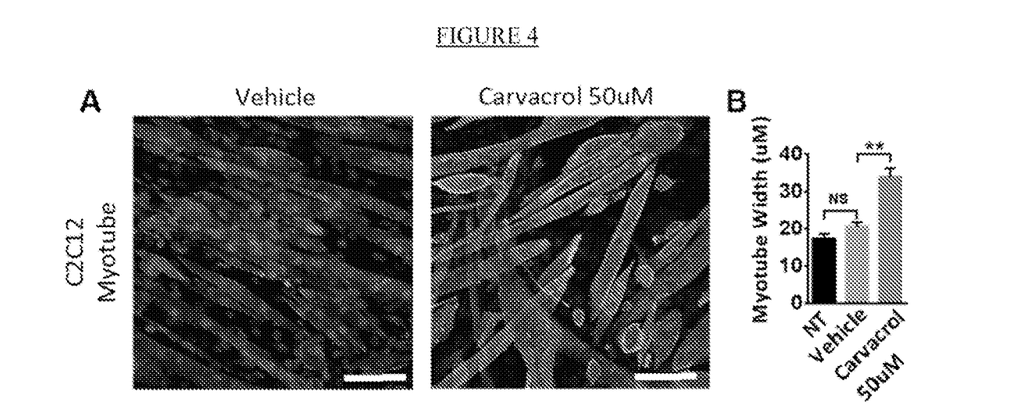
FIG. 4. A. Confocal images immunostained C2C12 myotubes (staining skeletal actin and Topro-3 nuclear stain) incubated for 48 hrs in vehicle (left) or carvacrol 50 µM (right). B. quantification of myotube width. NT—not treated, Vehicle—DMSO.

It was next examined whether the increase in cytosolic $Ca^{2+}$ induced by this class of compounds could induce cellular hypertrophy in vitro in C2C12 myotubes as would occur with augmented $Ca^{2+}$ release during exercise. Immunostaining and confocal imaging of C2C12 myotubes were performed as described previously in cardiac myocytes (Sah R., et al., The Timing of Myocardial Trpm7 Deletion during Cardiogenesis Variably Disrupts Adult Ventricular Function, Conduction and Repolarization. Circulation. 2013). It was found that carvacrol, applied at a concentration of 50 μM for 48 hours could induce significant myotube hypertrophy, as assessed by an increase in myotube diameter (FIG. 4).

Figure 5:
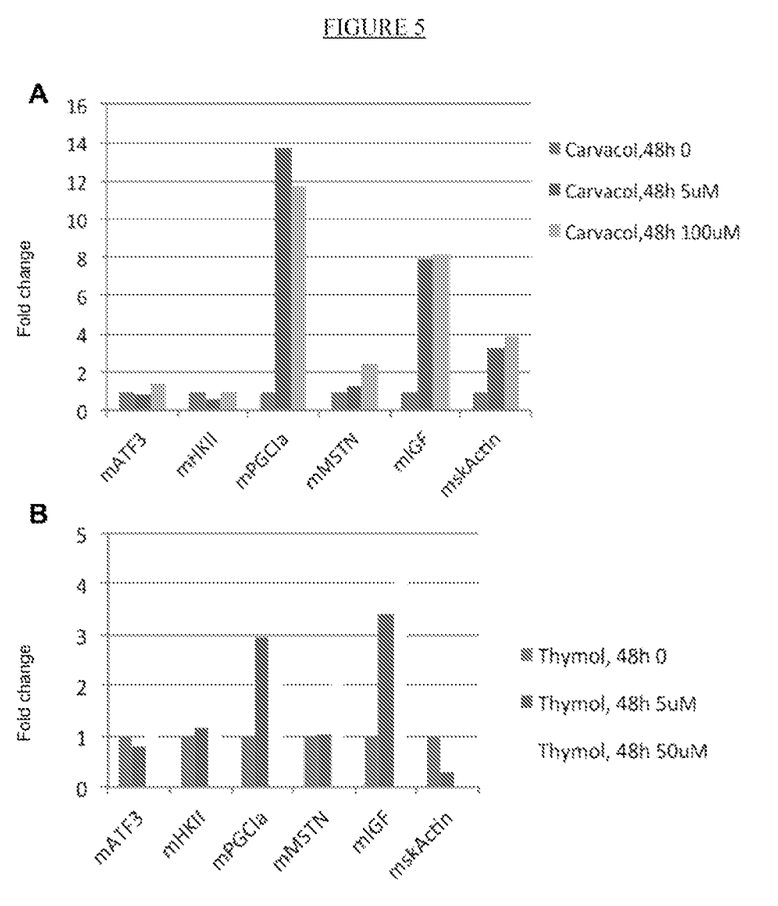
FIG. 5. Transcriptional analysis of candidate genes in C2C12 myotubes typically induced during skeletal muscle growth. A. fold change after 48 hrs carvacrol (0, 5, and 100 µM, from left to right for each grouping); and B. thymol (0, 5, and 50 µM, from left to right for each grouping).

A qRT-PCR based transcriptional screen was then performed to assess for induction of the classical genes associated with exercise-induced changes in skeletal muscle, including growth, and enhanced endurance (FIG. 5). Transcriptional analysis of candidate genes was performed as described previously (Sah R., et al., The Timing of Myocardial Trpm7 Deletion during Cardiogenesis Variably Disrupts Adult Ventricular Function, Conduction and Repolarization. Circulation. 2013; Sah R., et al., Ion channel-kinase TRPM7 is required for maintaining cardiac automaticity. Proc Natl Acad Sci USA. 2013; 110:E3037-46) using the following primers:

```
                                        (SEQ ID NO: 13)
TRPV1-F: CCG GCT TTT TGG GAA GGG T (SEQ ID NO: 14)
TRPV1-R: GAG ACA GGT AGG TCC ATC CAC (SEQ ID NO: 15)
TRPV2-F: TGC TGA GGT GAA CAA AGG AAA G (SEQ ID NO: 16)
TRPV2-R: TCA AAC CGA TTT GGG TCC TGT (SEQ ID NO: 17)
TRPV3-F: ACG GTC ACC AAG ACC TCT C (SEQ ID NO: 18)
TRPV3-R: GAC TGT TGG GAT TGG ATG GGG (SEQ ID NO: 19)
TRPV4-F: ATG GCA GAT CCT GGT GAT GG (SEQ ID NO: 20)
TRPV4-R: GGA ACT TCA TAC GCA GGT TTG G
```

It was found that both carvacrol and thymol significantly induced both PGC1α (a master regulator of mitochondrial biogenesis (Ruas, J. L., et al., Cell, 2012, 151(6), 319-31) 13.8-fold, carvacrol and 3-fold, thymol, and IGF-1 (a well established activator of skeletal muscle hypertrophy) (Rugs, J. L., et al., Cell, 2012, 151(6), 1319-1331; and Adams, G. R., J Appl Physiol (1985), 2002, 93(3), 1159-1167) ~8-fold carvacrol and ~4-fold thymol) in C2C12 myotubes.

Figure 6:
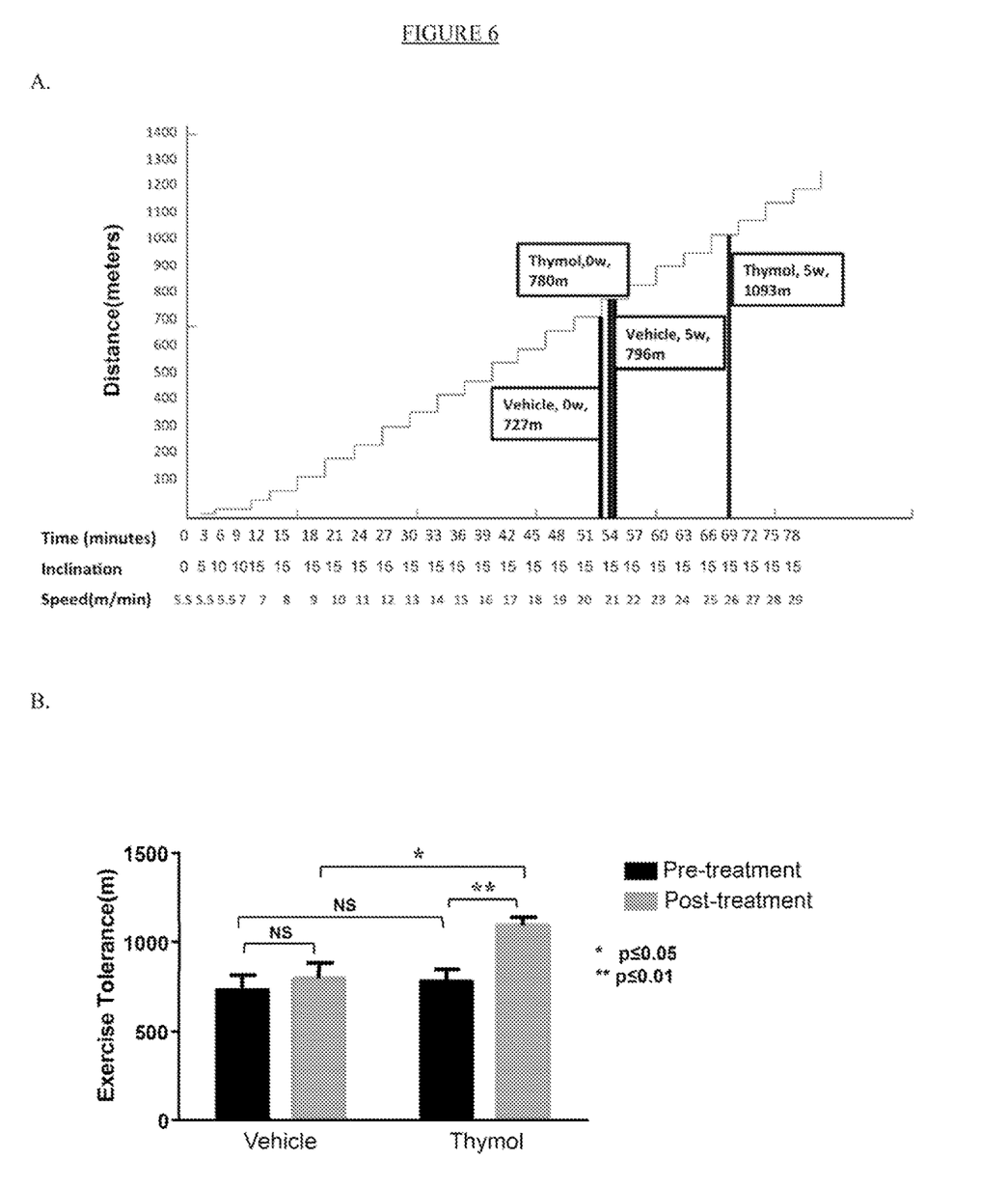
FIG. 6. Exercise tolerance measured by treadmill testing of C57/B6 mice before and after 5 weeks of either vehicle or thymol (20 mg/kg/day). A. Exercise protocol and tolerance after vehicle or thymol. B. Mean exercise tolerance pre and post treatment.
Figure 7:
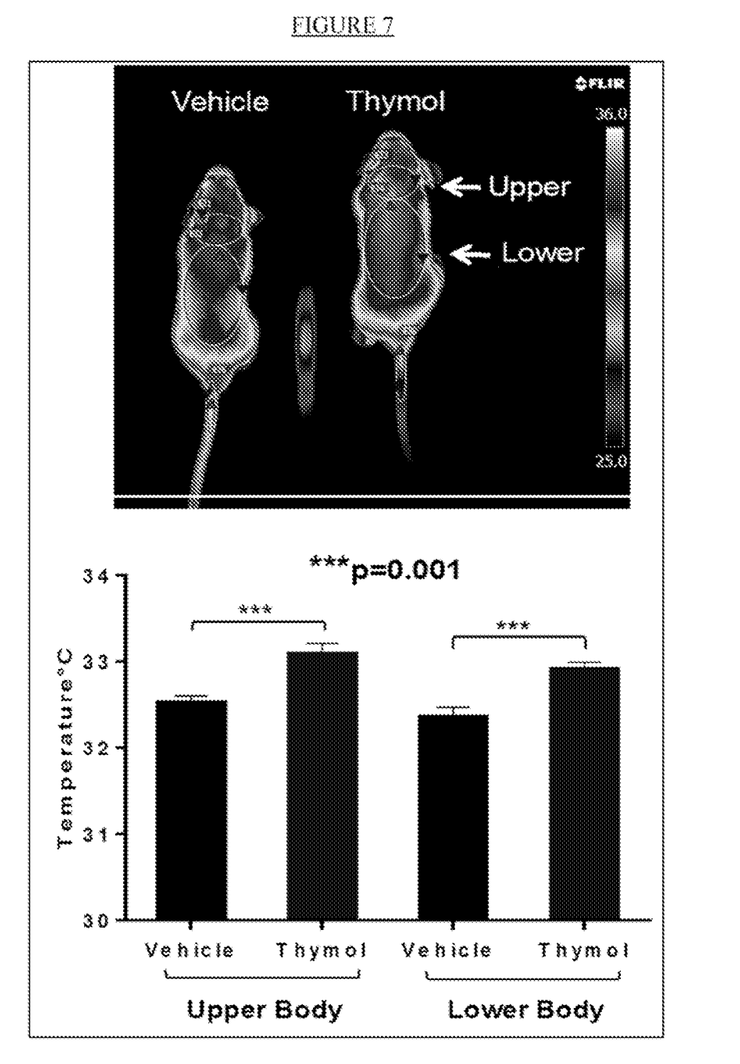
FIG. 7. Top: Representative thermal images of vehicle (left) and thymol (right) treated mice. Bottom: Mean data of temperature of upper and lower body in vehicle-treated vs thymol treated mice.
Figure 8:
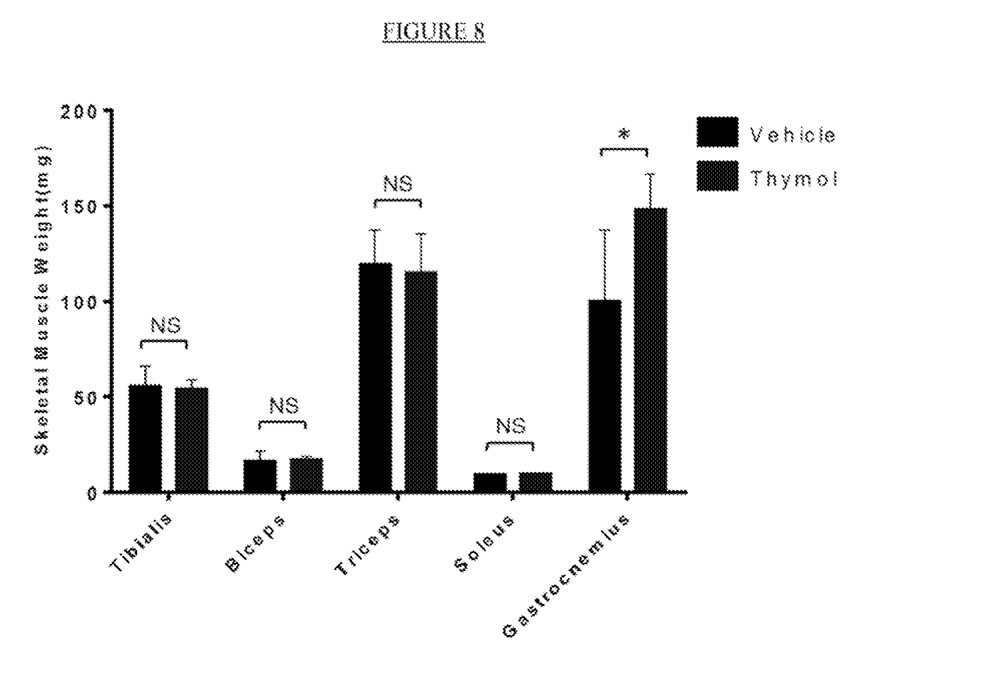
FIG. 8: Skeletal muscle weight in sedentary C57/B6 mice after 5 weeks of treatment with either vehicle or thymol (for each group, the left bar represents vehicle and the right bar represents thymol).
Figure 9:
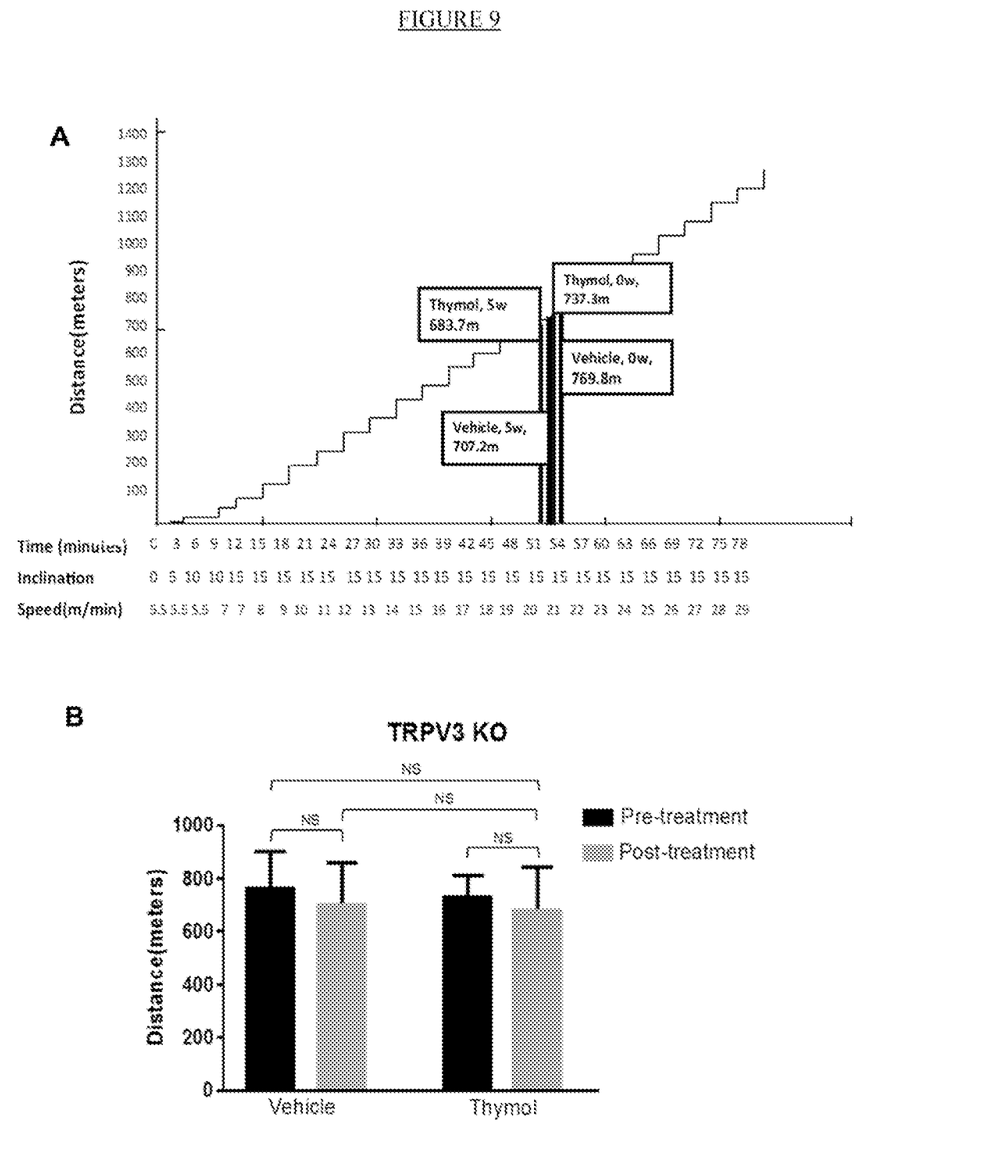
FIG. 9: Exercise tolerance measured by treadmill testing of TRPV3 KO mice before and after 5 weeks of either vehicle or thymol (20 mg/kg/day). A. Exercise protocol and tolerance after vehicle or thymol. B. Mean exercise tolerance pre and post treatment.

These data establish clear effects of thymol and carvacrol on $Ca^{2+}$ cycling in vitro in both cultured C2C12 myotubes and freshly isolated muscle fibers, and further demonstrates clear, robust effects on myotube hypertrophy and on induction of gene expression patterns characteristic of exercise-induced skeletal muscle remodeling (ie. PGC1α and IGF-1). Based on these strong in vitro data, in vivo studies were then performed to determine both safety and efficacy of using thymol and/or carvacrol to mimic the effects of exercise on skeletal muscle function. Based on the $Ca^{2+}$ imaging data, thymol appeared to be approximately twice as potent as carvacrol at augmenting cytosolic $Ca^{2+}$ in both C2C12 myotubes and freshly isolated mouse FDB fibers. Accordingly, the pilot studies were limited to thymol alone and treated sedentary C57/B6 mice with either vehicle (Sunflower oil) or Thymol (20 mg/kg/day) by oral gavage for 5 weeks and then assessed exercise capacity by treadmill testing, core body temperature by infra-red thermal imaging, and skeletal muscle hypertrophy by muscle weight. Exercise tolerance was performed using a treadmill and measured as previously described (Zingman L. V., et al., Kir6.2 is required for adaptation to stress. Proc Natl Acad Sci USA. 2002; 99:13278-83. Remarkably, it was found that thymol administration alone augmented exercise capacity of sedentary mice by 37% over vehicle treated mice (FIG. 6). This was also associated with a significant increase in core body temperature (thermal imaging was performed after slow ambulation on a treadmill, as described previously (Zhu Z., et al., Sarcolemmal ATP-sensitive potassium channels modulate skeletal muscle function under low-intensity workloads. J Gen Physiol. 2014; 143:119-34)) after mild exercise (FIG. 7) and an increase in gastrocnemius muscle weight (weight bearing muscles—FIG. 8). To determine whether this is a TRPV3-dependent effect the above in vivo experiments were repeated in TRPV3 knock-out mice (Cheng, X., et al., Cell, 2010, 141(2), 331-43) and found that the enhanced exercise capacity, augmented thermogenesis, and gastrocnemius hypertrophy conferred by thymol administration to wild-type mice was abolished upon genetic ablation of TRPV3 (FIG. 9, Exercise Tolerance only shown).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising modulating muscle atrophy, recovery, generation, or maintenance in a mammal in need thereof by systemically administering thymol or a pharmaceutically acceptable salt thereof to the mammal.

2. The method of claim 1 wherein the mammal is a human.

3. The method of claim 2 wherein the human is a chronically hospitalized patient.

4. The method of claim 2 wherein the human has been or will be immobilized for a period of several days or more.

5. The method of claim 2 wherein the human has cancer.

6. The method of claim 1, comprising modulating muscle atrophy in a mammal in need thereof by systemically administering thymol or a pharmaceutically acceptable salt thereof to the mammal.

7. The method of claim 1, comprising modulating muscle recovery in a mammal in need thereof by systemically administering thymol or a pharmaceutically acceptable salt thereof to the mammal.

8. The method of claim 1, comprising modulating muscle generation in a mammal in need thereof by systemically administering thymol or a pharmaceutically acceptable salt thereof to the mammal.

9. The method of claim 1, comprising modulating muscle maintenance in a mammal in need thereof by systemically administering thymol or a pharmaceutically acceptable salt thereof to the mammal.

* * * * *

SEQUENCE LISTING

<160> NUMBER OF SEQ ID NOS: 20

<210> SEQ ID NO 1
<211> LENGTH: 21

<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gctgccaagt gtcgaaacaa g                                                21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (4)..(4)
<223> OTHER INFORMATION: Inosine
<220> FEATURE:
<221> NAME/KEY: modified_base
<222> LOCATION: (6)..(6)
<223> OTHER INFORMATION: Inosine

<400> SEQUENCE: 2
cagntntcca atggcttcag g                                                21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
caagcgtgga ctgctcttcc                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgttgcagga tggctcggac                                                  20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
agccgtgacc actgacaacg ag                                               22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic primer -continued

```
<400> SEQUENCE: 6
gctgcatggt tctgagtgct aag                                              23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtacgacgt ccagagggat                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgccatccg cttgcattag                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgatgggga aaatcagcag                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgccaggtag aagaggtgtg                                                  20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tccaagtcct gcaagtgaac a                                                21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
gtcaggatac ctcgcttgct                                              20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccggcttttt gggaagggt                                               19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagacaggta ggtccatcca c                                            21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgctgaggtg aacaaaggaa ag                                           22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcaaaccgat ttgggtcctg t                                            21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acggtcacca agacctctc                                               19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

-continued

```
gactgttggg attggatggg g                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atggcagatc ctggtgatgg                                                20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaacttcat acgcaggttt gg                                             22
```